United States Patent [19]

Bunch

[11] 4,095,110
[45] June 13, 1978

[54] MEANS FOR STEPPING X-RAY RECEPTOR IN DIRECTION OPPOSITE TO POSITION CHANGE OF SOURCE

[75] Inventor: Laverne R. Bunch, Baltimore, Md.

[73] Assignee: CGR Medical Corporation, Baltimore, Md.

[21] Appl. No.: 739,017

[22] Filed: Nov. 4, 1976

[51] Int. Cl.² ............................................. A61B 6/02
[52] U.S. Cl. ............................. 250/445 T; 250/445 R
[58] Field of Search ............... 250/452, 445 T, 445 R, 250/447, 360; 318/696

[56] References Cited

U.S. PATENT DOCUMENTS 3,091,691  5/1963  Snow ................................. 250/444
3,766,387  10/1973  Heffan et al. ..................... 250/360

Primary Examiner—Alfred E. Smith
Assistant Examiner—T. N. Grigsby
Attorney, Agent, or Firm—Brady, O'Boyle & Gates

[57] ABSTRACT

A bucky translated under an X-ray table in radiographic apparatus of the linear tomography type wherein precise positioning with respect to the X-ray tubestand is achieved by a combination of a ball screw drive attached to the bucky and a permanent magnet stepper motor coupled thereto which incrementally rotates one step with each input drive pulse applied thereto from a pulse generator operated in accordance with a control input applied from an electronic control system in response to the sensed position change of the tubestand.

9 Claims, 3 Drawing Figures

MEANS FOR STEPPING X-RAY RECEPTOR IN DIRECTION OPPOSITE TO POSITION CHANGE OF SOURCE

CROSS-REFERENCE TO RELATED APPLICATION

The present invention is related to U.S. Ser. No. 724,641, filed Sep. 20, 1976, entitled "Tomography System," M. J. Hellstrom, et al., which application is also assigned to the present assignee.

BACKGROUND OF THE INVENTION

This invention relates generally to diagnostic X-ray apparatus and more particularly to a motor driven bucky which is adapted to translate with increased positional precision and velocity.

An electronic linear tomography system such as disclosed in the above-referenced related application requires precise position and speed regulation of the bucky for its operation. Previously, the bucky was either non-motorized or lacked the required performance of motorized designs. Where for example positional requirements of ±0.025mm error over a 50cm travel exit and where the velocity requirements were 0 to 3600rpm speed regulation, a conventional servo system with feedback becomes prohibitively expensive while other mechanical drives are not capable of meeting the aforesaid design criteria.

It is an object of the present invention, therefore, to provide a new and improved bucky drive which is not only simple in design, but eliminates the need for braking devices, as well as providing the ability to be manually positioned.

SUMMARY

Briefly, the subject invention is directed to a means in a linear tomographic system for translating a bucky type X-ray film holder with precise position and speed regulation relative to the X-ray tube in accordance with a positional control signal developed from the sensed position of the X-ray tube and comprises the improvement of a bucky attached to a ball screw shaft by means of ball screw nut means with the ball screw shaft being coupled to a permanent magnet stepper motor having an output shaft which rotates incrementally in response to electrical pulses generated in response to said positional control signal.

DESCRIPTION OF THE PREFERRED EMBODIMENT

Figure 1:
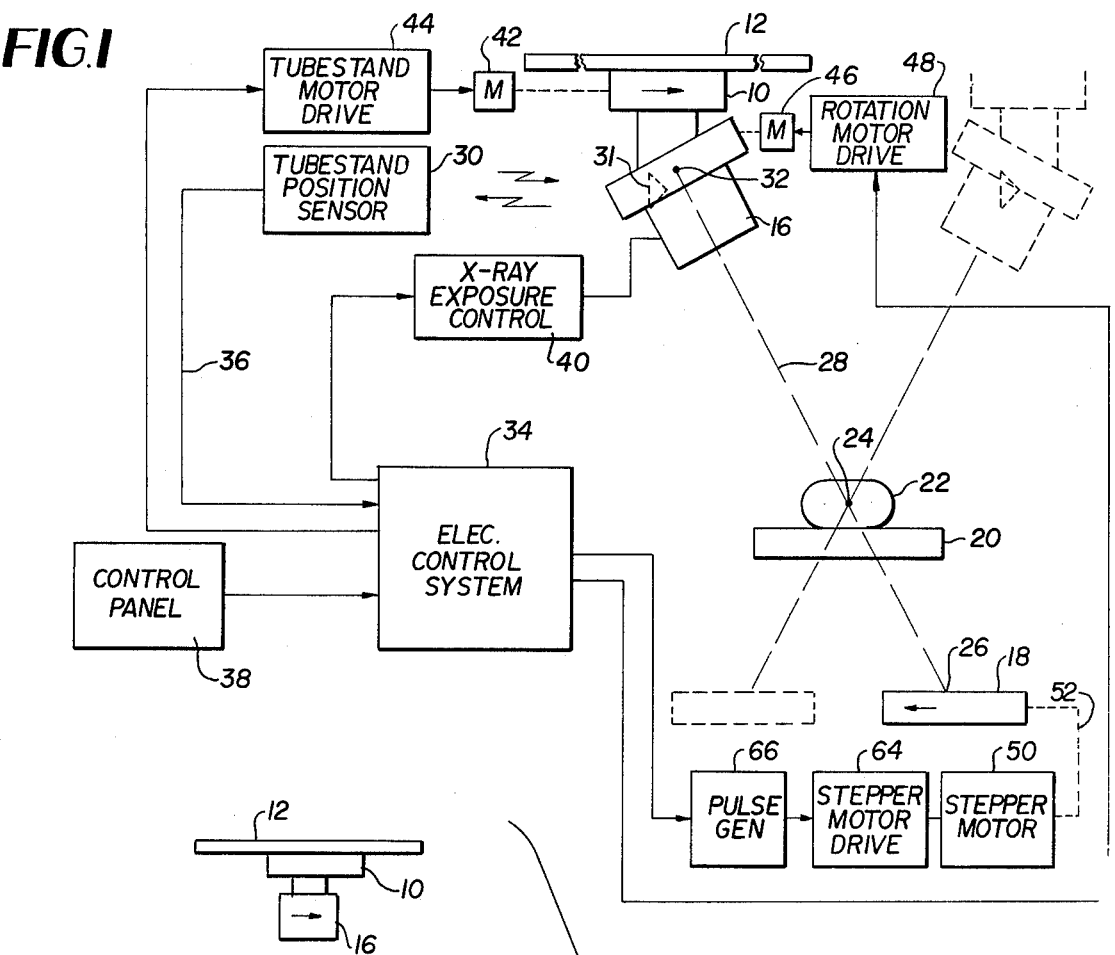
FIG. 1 is a block diagram illustrative of a linear tomographic system incorporating the subject invention.

Referring now to the drawings, reference numeral 10 denotes an X-ray tube suspension system commonly referred to as a tubestand which for purposes of illustration is mounted for translational movement on a ceiling attached assembly 12 and includes an X-ray tube 16 directed to a movable X-ray film holder commonly referred to as a bucky 18 located beneath an X-ray examination table 20 upon which a patient 22 or other object under examination is located. As is well known in a tomographic procedure, the tubestand 10 including the X-ray tube 16 and the bucky 18 which contains the X-ray film are moved or translated in mutually opposite linear directions with the tube rotating in order to maintain a constant point or fulcrum 24 in space within the patient 22, which acts to accurately define an image location 26 on the film in response to the X-ray beam 28 passing through the patient while blurring the surrounding image region.

In order to provide a non-mechanical linear link or coupling between the X-ray tube 16 and the bucky 18 so that the central ray of the X-ray beam 28 always points to the same location on the bucky 18, a tubestand position sensor unit 30 is optically coupled to an optical reflector member 31 in the form of a corner cube prism which is located at a spot which is fixed relative to the focal spot 32 of the X-ray tube 16. The tubestand position sensor unit 30 is shown in detail in the above-referenced related application and comprises a helium neon laser, not shown, which produces a monochromatic light beam which is directed to the reflector 31 through a beam expander, and interferometer assembly.

The tubestand position and more particularly the linear translation of the tubestand 10 results in an interferometer fringe pattern which is converted to an electrical pulse signal which in turn is coupled to an electronic control system 34 by means of electrical signal coupling means 36. The control system 34 operates in response to operator selected input parameters from a control panel 38 which parameters, for example, comprise fulcrum level, speed of sweep, and angle of sweep to first generate a control signal for operating an electrical drive motor 42 through a tubestand motor drive unit 44 for linearly translating the tubestand 10 to a START position and then in a predetermined sweep direction. The control system 34 responds to the pulse signals from the sensor unit 30 to control a second electrical motor 46 through a rotation motor drive unit 48 for rotating the X-ray tube 16 during the tomographic sweep and a third but particular type of electrical motor 50 for translating the bucky 18 in response to the movement of the tubestand 10.

Figure 2:
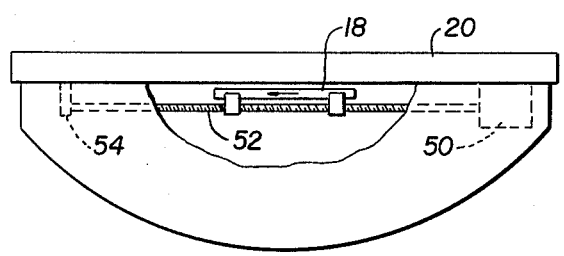
FIG. 2 is a simplified plan view of tomographic apparatus further illustrative of the subject invention incorporated therein.
Figure 3:
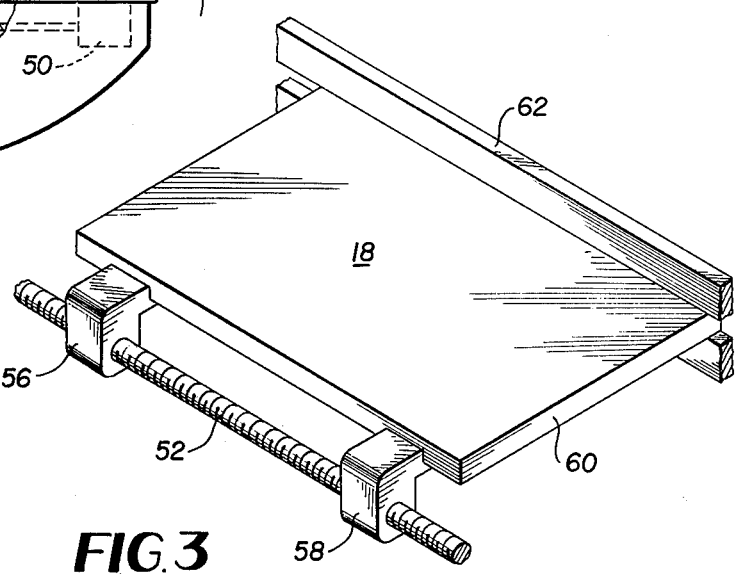
FIG. 3 is a perspective view of a bucky type film holder coupled to a ball screw shaft for translational movement thereby.

As noted above, in a tomographic procedure the tubestand 10 moves in an opposite direction in relation to the bucky 18. The latter accordingly must follow the movement of the tubestand with great precision. Heretofore, a mechanical tie-bar linkage typically connected the bucky to the X-ray tube. In order to eliminate the tie-bar linkage and obtain a positional type of servo operation without elaborate feedback networks, the present invention utilizes a permanent magnet stepper motor for the motor 50 and ball screw drive for translating the bucky 18. This arrangement is furthermore disclosed in FIG. 2 wherein the stepper motor 50 is directly connected to one end of an elongated ball screw shaft 52 which terminates in a bearing assembly 54 beneath the X-ray examination table 20. The ball screw shaft 52 runs lengthwise under the X-ray table 20 and couples to the bucky 18 by means of a pair of ball screw nuts 56 and 58 as shown in FIG. 3 which are attached to the bucky frame generally designated by reference numeral 60. The bucky frame 60, moreover, is constrained by simple translational guide means 62 so that any rotation of the ball screw shaft 50 effects translational movement of the bucky back and forth lengthwise under the X-ray table 20.

The stepper motor 50 is fed electrical drive pulses of first and second directional polarities from a drive unit 64 coupled to a pulse generator 66 under the control of the electronic control system 34. The stepper motor 50 precisely rotates one increment of motion with each input drive pulse supplied thereto. With the motor 50 directly connected to the ball screw shaft 52, the result is precise translation in a predetermined direction in incremental steps according to the polarity of square wave type drive pulse signals generated in response to tubestand translation sensed by the position sensor unit 30.

Typically the stepper motor 50 comprises a permanent magnet stepper motor having an input response of, for example, 10,000 steps per second with no loss of steps and provides one revolution for each 200 steps. The ball screw shaft 52 has 0.5 inch thread diameter and a 0.200 inch per revolution pitch.

As taught in the aforementioned related application, the laser type tubestand position sensor is adapted to generate a pulse train in the order of $12 \times 10^6$ pulses per each inch of translation of the tubestand 10. This pulse rate is divided by a predetermined frequency division in the electrical control system 34 where it is then applied to the pulse generator 66 in one of two polarities for driving the stepper motor 50 forward or backward as required.

Since the stepper motor 50 has a unique inherent braking capability, no other external braking means are required while yet permitting free wheeling when unenergized so that the bucky 18 can be moved manually at will. The latter movement presents no problem, since at the beginning of a tomographic procedure the electical control system 34 is operative to drive the tubestand 10 to the START position via its translational drive motor 42 and its associated drive unit 44. This movement back to the START position will still be sensed by the sensor unit 30, causing the electrical control system 34 in turn to couple control signals to the pulse generator 66 which supply pulses of proper polarity to the stepper motor 50 to cause the bucky to assume its respective START position, whereupon the tube and the bucky 18 will be in line prior to the beginning of a tomographic sweep.

The ball screw nuts 56 and 58 are prestressed for zero play, which is adapted to simplify alignment in a manner unobtainable heretofore. Also the inherent characteristics of a permanent magnet stepper motor results in improved damping characteristics to reduce noise during stepping, as well as providing high torque at relatively high speeds. This permits translation while the X-ray table 20 is in a vertical position without a counterweight system.

While the subject apparatus disclosed is relatively simple, it provides a high performance unobtainable in present motorized and non-motorized designs having relatively complicated bucky brackets, wheels, bearings and guiderails. Electronic control, moreover, is a minimum yet extremely accurate positioning of the bucky 18 relative to the position of the X-ray tube 16 is obtained without the requirement of a mechanical linkage therebetween.

While there has been shown and described what is at present considered to be the preferred embodiment of the subject invention, modifications will readily occur to those skilled in the art. For example, when desirable, a stepper motor and its attendant drive circuitry may be utilized for translating the tubestand and/or rotating the X-ray tube. It is not desired, therefore, that the invention be limited to the specific arrangements shown and described, but it is to be understood that all equivalents, alterations, and modifications coming within the spirit and scope of the present invention are herein meant to be included. Accordingly,

I claim as my invention:

1. Apparatus for translating X-ray receptor means such as a film holder relative to the X-ray source in diagnostic X-ray apparatus a typical example of which is a linear tomography system, comprising the improvement of:
   an elongated ball screw shaft positioned to provide translational movement of said X-ray receptor means in a predetermined direction when rotated;
   ball screw nut means threaded on said shaft and attached to said X-ray receptor means;
   an electrical stepper motor having a rotary output shaft coupled to said ball screw shaft and being responsive to drive pulses applied thereto to incrementally rotate said output shaft for each drive pulse applied; and
   drive pulse circuit means coupled to said stepper motor and being operable to generate said drive pulses in response to a position change of said X-ray source, said drive pulse circuit means including electrical pulse generator means providing electrical drive pulses of predetermined polarity for operating said stepper motor to rotate said ball screw shaft in a direction which translates said X-ray receptor means in an opposite direction with respect to the direction of the position change of said X-ray source.

2. The apparatus as defined by claim 1 wherein said ball screw shaft is directly connected to said output shaft of said stepper motor.

3. The apparatus as defined by claim 1 and additionally including X-ray examination table means having a top, wherein said ball screw shaft and said electrical stepper motor are located beneath said top, and wherein said stepper motor is directly connected to one end of said ball screw shaft and additionally including bearing means coupled to the opposite end of said screw shaft.

4. The apparatus as defined by claim 3 wherein said ball screw shaft is oriented lengthwise of said table.

5. The apparatus as defined by claim 1 and additionally including sensor means selectively located in the vicinity of said X-ray source and being operable to provide an electrical output signal indicative of the position change of said X-ray source, and wherein said pulse generator means operates in response to the sensor output signal to generate said drive pulses.

6. The apparatus as defined by claim 5 and additionally including control circuit means coupled to said sensor means and being responsive to said output signal therefrom to provide an electrical control signal coupled to said pulse generator means.

7. The apparatus as defined by claim 6 and additionally including stepper motor drive means coupled between said pulse generator and said stepper motor.

8. The apparatus as defined by claim 6 wherein said stepper motor comprises a permanent magnet stepper motor.

9. The apparatus as defined by claim 6 wherein said X-ray source is located in a tubestand adapted to be translated by an electrical motor having drive means coupled thereto and operated in response to a control signal applied thereto from said control circuit means, and wherein said X-ray receptor means comprises a bucky type of film holder.

* * * * *